United States Patent
Zurlo et al.

(10) Patent No.: US 11,884,702 B2
(45) Date of Patent: *Jan. 30, 2024

(54) SYSTEMS AND METHODS FOR PROCESS SCALE ISOLATION OF IMMUNOGLOBULIN G

(71) Applicant: Plasma Technologies, LLC, Charleston, SC (US)

(72) Inventors: Eugene Zurlo, Charleston, SC (US); Dennis Curtin, Charleston, SC (US); Klaus Peter Radtke, Apex, NC (US); Ryan Dorfman, Essex, VT (US); Matthew Whelihan, Colchester, VT (US)

(73) Assignee: Plasma Technologies, LLC, Charleston, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 17/560,163

(22) Filed: Dec. 22, 2021

(65) Prior Publication Data
US 2022/0204556 A1 Jun. 30, 2022

Related U.S. Application Data

(60) Provisional application No. 63/272,605, filed on Oct. 27, 2021, provisional application No. 63/208,778, filed on Jun. 9, 2021, provisional application No. 63/131,097, filed on Dec. 28, 2020.

(51) Int. Cl.
| | | |
|---|---|---|
| *C07K 1/30* | (2006.01) | |
| *C07K 1/22* | (2006.01) | |
| *C07K 1/36* | (2006.01) | |
| *C07K 1/18* | (2006.01) | |
| *C07K 16/06* | (2006.01) | |

(52) U.S. Cl.
CPC .............. *C07K 1/303* (2013.01); *C07K 1/22* (2013.01); *C07K 1/36* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 6,069,236 A | 5/2000 | Burnouf-Radosevich | |
| 7,879,331 B2 * | 2/2011 | Zurlo | A61P 7/00 424/177.1 |
| 7,879,332 B2 * | 2/2011 | Zurlo | A61M 1/3696 424/177.1 |
| 8,063,189 B2 | 11/2011 | Arunakumari | |
| 9,096,648 B2 | 8/2015 | Bian | |
| 9,556,253 B2 | 1/2017 | Nuvula | |
| 10,815,270 B1 | 10/2020 | Zurlo | |
| 2007/0049733 A1 * | 3/2007 | Zurlo | C07K 14/765 530/387.1 |
| 2007/0173638 A1 * | 7/2007 | Buchacher | A61L 2/0011 530/387.1 |

FOREIGN PATENT DOCUMENTS

| | | | | |
|---|---|---|---|---|
| WO | 2011149472 | 12/2011 | | |
| WO | WO-2013126904 A1 * | 8/2013 | ............. | A61K 35/16 |
| WO | WO-2018019898 A1 * | 2/2018 | ............... | C07K 1/22 |

OTHER PUBLICATIONS

Gottschalk "Bioseparation in antibody manufacturing: the good, the bad and the ugly" Biotechnol. Prog. 2008, 24, 496-503 (Year: 2008).*
Matulis "Selective precipitation of proteins" Current Protocols in Protein Science, 4.5.1-4.5.37, Feb. 2016 (Year: 2016).*
International Search Report dated Apr. 15, 2022 from related PCT application No. PCT/US2021/065017. 8 pages.

* cited by examiner

*Primary Examiner* — Daniel E Kolker
*Assistant Examiner* — James L Rogers
(74) *Attorney, Agent, or Firm* — Fish IP Law, LLP

(57) ABSTRACT

Methods are provided for isolation of immunoglobulin G (IgG) from plasma, where IgG is initially fractioned by salt precipitation, followed by successive ion exchange steps in which IgG appears in unbound, flow-through fractions of the ion exchange steps. Some embodiments employ successive anion exchange steps. Other embodiments employ an anion exchange step followed by application of flow-through of the anion exchange step to a cation exchange step, with IgG collected in flow-through fractions from the cation exchange step. IgG is collected at high yield (typically about 75% or greater) and high purity. Avoidance of binding and elution from chromatography media simplifies processing and scale up without sacrificing IgG quality or yield.

18 Claims, 13 Drawing Sheets

SYSTEMS AND METHODS FOR PROCESS SCALE ISOLATION OF IMMUNOGLOBULIN G

This application claims the benefit and U.S. Provisional Patent Application No. 63/131,097 filed on Dec. 28, 2020, U.S. Provisional Patent Application No. 63/208,778, filed Jun. 9, 2021, and U.S. Provisional Patent Application No. 63/272,605, filed Oct. 27, 2021. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is isolation of immunoglobulin G (IgG), particularly from serum and/or plasma.

BACKGROUND

The background description includes information that may be useful in understanding the present invention. It is not an admission that any of the information provided herein is prior art or relevant to the presently claimed invention, or that any publication specifically or implicitly referenced is prior art.

Immunoglobulin G (IgG) is a protein product prepared from human blood plasma for the treatment of primary immunodeficiency and a wide variety of other immunological disease conditions. In addition, IgG can be used for passive immune transfer to accelerate the clearance of pathogens (e.g., SARS-CoV2) and prevent or treat infection. For over 70 years, IgG has been produced with the Cohn process, which separates, or fractionates, plasma proteins based on their differential solubility in ethanol with variances in temperature, pH, ethanol concentration, ionic strength, and protein concentration. While the overall IgG yield from the Cohn process is not generally disclosed by commercial plasma fractionators, the modern Cohn process is widely believed to achieve yields of only about 50-60% of the IgG present in the starting material. In addition, it is understood that this process takes approximately 7 to 10 days to complete.

U.S. Pat. No. 7,879,331, to Zurlo et al., describes a method for isolation of IgG that utilizes successive fractionation of plasma using citrate salts to yield a precipitate that contains IgG. Following dissolution and buffer exchange, the resulting IgG-rich solution is treated by ion exchange chromatography to generate an eluate that contains the IgG. This eluted fraction is further subjected to anion exchange chromatography. Unfortunately, this process can result in rapid fouling of diafiltration membranes if this technique is utilized for buffer exchange into buffers suitable for the ion exchange steps. This limits the scale at which diafiltration can be applied. In addition, binding and subsequent elution of IgG from the ion exchange media inevitably results in loss of the protein.

Thus, there is still a need for rapid, efficient, and scalable methods for isolation of IgG at high yield and purity.

SUMMARY OF THE INVENTION

The inventive subject matter provides compositions, methods, and systems that provide isolation of immunoglobulin G (IgG) or other proteins (e.g., albumin, AAT) at both high purity and high yield. Such methods utilize successive ion exchange steps in which IgG remains in flow-through fractions, avoiding the need for elution steps. Avoidance of conventional binding, washing, and elution steps simplifies processing and scale up processes while also increasing yield. In addition, non-IgG proteins can be isolated from various waste streams of the process (e.g., bound fractions from ion exchange steps).

One embodiment of the inventive concept is a method for isolating a protein (e.g., IgG) from a solution (e.g., plasma, a product of a separation step) by adding a salt (such as a citrate or acetate salt) to the solution to generate a supernatant and a precipitate, dissolving the precipitate in an aqueous solution to generate a dissolved precipitate that includes the protein and at least one contaminant, applying the dissolved precipitate to an anion exchange media to generate a first bound fraction and a first flow-through (where the first flow-through includes the protein and a contaminant), and applying the first flow-through to a cation exchange media that can bind both the protein and the contaminant to generate a second bound fraction that includes the contaminant and a second flow-through that includes the protein. In such methods the capacity of the cation exchange media is selected such that less than about 3% (in clued range??? 3-10%) of content of the protein in the solution is lost during the cation exchange step. In some of such embodiments the protein is immunoglobulin G, and the contaminant can be Factor XI or activated Factor XI. In such methods the cation exchange media can be provided as a particle, bead, or filter. In some of such embodiments caprylate is added to the dissolved precipitate, which can be followed by comprising removing solids. Such solid removal can be accomplished using a depth filter that is selected to retain Factor XI and/or Factor XII, such as a depth filter that includes diatomaceous earth. Such a depth filter can exclude perlite. Yield of protein from such a method can be 70% or more (relative to the amount of protein in the starting protein solution). In some embodiments one or more additional proteins are recovered from the supernatant from the salt addition step.

Another embodiment of the inventive concept is a system for isolating a protein (e.g., IgG) from a solution (e.g., plasma or a fraction obtained from plasma). Such a system includes a fractionation module configured to receive the solution and perform salt fractionation generating a supernatant and a precipitate, separating the supernatant from the precipitate, and providing the precipitate as a first output. It also includes a first separation module comprising an anion exchange medium and connected to the first output, and that has a second output for a flow-through fraction (which includes the protein and at least one contaminant). A second separation module is provided that includes cation exchange media that binds the contaminant (e.g., Factor XI and/or activated Factor XI), and has a third output for a second flow-through fraction that includes the protein. This second separation module includes an amount of the cation exchange media that provides a cation exchange capacity such that less than 3% (range 3-10%) of content of the protein in the blood product is lost during the cation exchange step. Such a system can include a viral inactivation module within the fluid path between the fractionation module and the first separation module. In some embodiments a depth filter is interposed between the first output and the first separation module. Such a depth filter can be selected to retain Factor XI and/or Factor XII, and can include diatomaceous earth. In some of such embodiments the depth filter can exclude perlite.

Another embodiment of the inventive concept is a method for isolating a protein (e.g., IgG, albumin, AAT) from a solution (e.g., plasma or a product of an isolation step) by adding a salt (e.g., citrate or acetate) to the solution to generate a supernatant and a precipitate (where the supernatant includes the protein and at least one contaminant), applying the supernatant to an anion exchange media to generate a first bound fraction and a first flow-through (where the first flow-through includes the protein and a contaminant), and applying the first flow-through to a cation exchange media to generate a second bound fraction that includes the contaminant and a second flow-through that includes the protein. Capacity of the cation exchange media is selected so that less than about 3% (range 3-10%???) of content of the protein in the solution is lost on cation exchange. The cation exchange media can be provided as a particle, bead, or filter. In some of such embodiments caprylate is added to the dissolved supernatant, which can be followed by removing solids from the resulting solution. Such solids can be removed using a depth filter that includes diatomaceous earth; in some embodiments perlite is excluded from such a depth filter. Typically yield of the protein (e.g., IgG) is 70% or greater (relative to content of the protein in the solution) or greater. In some embodiments one or more additional proteins can be recovered from the precipitate.

Another embodiment of the inventive concept is a system for isolating a protein (e.g., IgG, albumin, AAT) from a solution (such as plasma or a fraction derived from plasma), which includes a fractionation module that receives the solution and performs a salt fractionation step to generate a supernatant and a precipitate and also separates the supernatant from the precipitate and provides the supernatant to a first output. The system also includes a first separation module that includes an anion exchange medium, where the first separation module receives the first output and provide a second output that includes a flow-through fraction (which includes the protein and at least one contaminant). The second output is directed to a second separation module that includes a cation exchange media that can bind the contaminant and the protein and that provides a third output that includes a second flow-through fraction that includes the protein. The second separation module includes an amount of the cation exchange media that provides a capacity selected so that less than about 3% (range 3-10%???) of content of the protein in second output is lost on in the cation exchange step. Such a system can include a viral inactivation module within a fluid path between the fractionation module and the first separation module.

Another embodiment of the inventive concept is a method of isolating immunoglobulin G, by adding a citrate salt to an aqueous solution comprising immunoglobulin G (IgG) present in two or more IgG subclasses to a give a concentration of at least 11% by weight, to generate a first supernatant and a first precipitate. The first supernatant is separated from the first precipitate, and additional citrate added to the first supernatant to a concentration of 22-26% by weight, thereby generating a second supernatant and a second precipitate. The second precipitate is separated from the second supernatant and dissolved. Conductivity of the dissolved second precipitate is adjusted to 5 mS to 10 mS (e.g., about 7 mS) to form a diluted protein solution. This diluted protein solution is applied to a first ion exchange column that includes an anion exchange media (e.g., one containing a quaternary amine) to generate a first flow-through, which is in turn applied to a second ion exchange column that includes the anion exchange media to generate a second flow-through. The first and second anion exchange columns can be arranged in series. Alternatively, the first flow-through can be collected and pooled, then applied to the second anion exchange column. This second flow-through includes the IgG, and also provides at least partial separation of two or more immunoglobulin classes or IgG subclasses. The resulting IgG has a purity of at least about 85% by weight. In some of such embodiments a fatty acid (e.g., a fatty acid having a carbon chain with 4 to 10 carbons) is added to the dissolved second precipitate to form a suspension, which can in turn be applied to a depth filter. Composition and size of the depth filter are selected to avoid activation of clotting factors present in the dissolved second precipitate and to reduce the concentration of clotting factors in material passing through the filter. In some of such embodiments the second flow-through fraction can be further processed by applying it to a cation exchange medium (e.g., one containing a sulfonate and/or a carboxylic acid group) under conditions in which IgG binds and remains bound to the cation exchange medium. The cation exchange medium is then washed, and IgG subsequently eluted from the cation exchange medium.

Another embodiment of the inventive concept is a pharmaceutical composition that includes immunoglobulin G (IgG) at a concentration of at least 40 mg/mL and immunoglobulin A at a concentration of less than 2 μg/mL, where the IgG has a purity of greater than 98% and has not been eluted from a chromatography media. In some embodiments such a pharmaceutical composition contains less than 1 mU/mL of activated Factor XI. In some embodiments such a pharmaceutical composition contains less than 0.1 μg/mL of Factor XII. In some embodiments the IgG content of the pharmaceutical composition is isolated from at least 2 L of plasma.

Various objects, features, aspects and advantages of the inventive subject matter will become more apparent from the following detailed description of preferred embodiments, along with the accompanying drawing figures.

DETAILED DESCRIPTION

Figure 1:
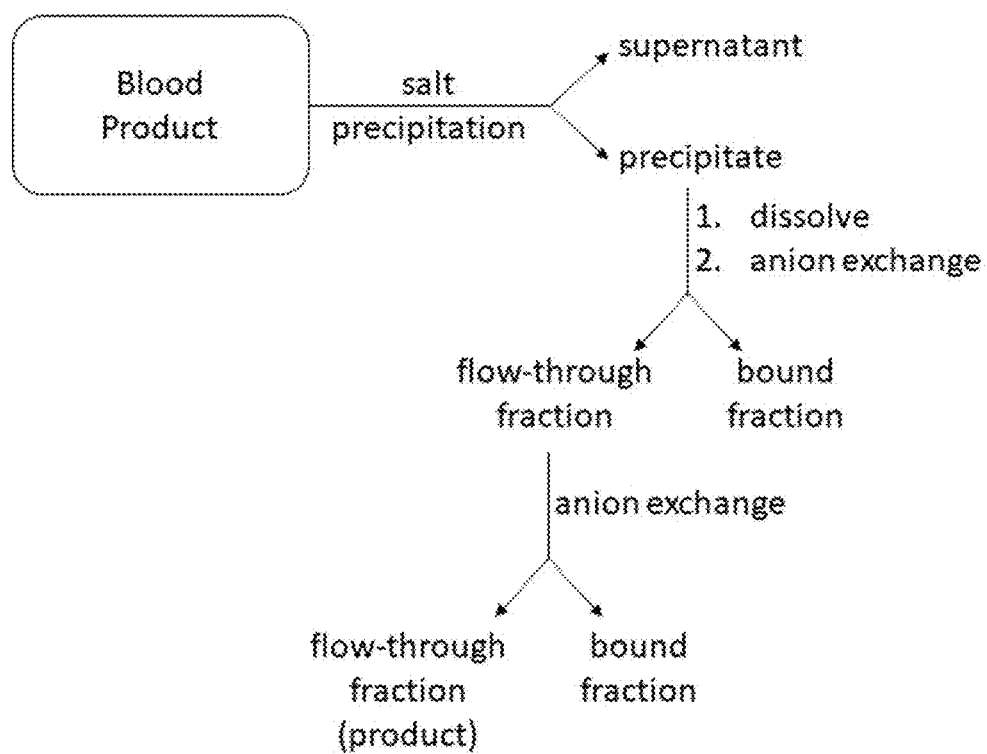
FIG. 1 schematically depicts an exemplary process of the inventive concept utilizing two anion exchange steps in succession.

The Inventors have developed a commercially scalable process that can provide an IgG yield of approximately 75% to 80% or more while meeting the purity standards set by the FDA for a commercial product. This compares to an IgG 50-60% yield of the current Cohn Process. The process also dramatically reduces contamination by Factor XI, Factor XII, and/or IgA in the final product, and can reduce such contamination to levels that are currently undetectable.

One should appreciate that the disclosed techniques provide many advantageous technical effects including rapid provision of immunoglobulin G at high purity and high yield at process scale.

The Inventors process produces a more native IgG since the process eliminates the use of alcohol and minimizes denaturing conditions (e.g., extreme pH changes, etc.). In addition, in the claimed process IgG is not hound and subsequently eluted from chromatography media. This advantageously both enhances yield and reduces the chance of denaturation, while also simplifying the isolation process and greatly reducing processing time. As such these processes are distinct and different from (and much more cost effective than) current IgG isolation processes, and can provide an IgG product with improved protein stability, increased in vivo half-life, more rapid infusion rates, improved patient tolerance, and reduced immunogenicity. The Inventors' manufacturing process takes approximately two days to complete, compared to approximately 7 to 10 days for the Cohn process-dependent processes. The construction and operational costs for a manufacturing plant for this new process is projected a fraction of the cost of existing plants while also producing higher yields of other therapeutic proteins in their active and native form. Furthermore, no flammable/explosive chemicals are used, reducing capital investment, increasing worker safety, and reducing negative environmental impact. It should be appreciated that, while isolation of immunoglobulin G (IgG) is discussed herein, Inventors contemplate that other serum proteins of commercial value (e.g., AAT, albumin) can be isolated from various intermediate process streams (e.g., supernatants or precipitates from precipitation steps, materials bound to chromatography media, etc.).

Some embodiments of the inventive concept utilize two or more ion exchange chromatography steps having the same ion exchange effect (e.g., anion exchange) in succession, where buffer conditions and column binding capacity are selected or optimized to provide the target protein (e.g., IgG) in the flow-through fraction of each of the ion exchange chromatographic steps. Such ion exchange steps can be performed using media of similar capacity (e.g., similar or identical volumes of the same ion exchange media). Alternatively, in some embodiments ion exchange media of similar ion exchange function but different capacity (e.g., two different volumes of the same ion exchange media) can be used. Such ion exchange media can be arranged such that the flow-through fraction of a first volume or amount of ion exchange media can be directed to the inlet of a second volume of amount of ion exchange media. Alternatively, in some embodiments all or portions of the flow-through fraction of a first volume or amount of ion exchange media can be pooled prior to application to a second volume of amount of ion exchange media.

Embodiments of the inventive concept can utilize either anion or cation exchange chromatography, where buffer conditions and column binding capacity are selected or optimized to provide the target protein (e.g., IgG) in the flow-through fraction of each chromatographic step.

An example of a process of the inventive concept is shown in FIG. 1. It should be appreciated that in this context a blood product can be serum, plasma, cryo-poor plasma, cryo-poor plasma into which the cryoprecipitate has been re-dissolved, or a fraction (e.g., a chromatography eluate, a chromatography flow-through, a supernatant, or a dissolved precipitate) resulting from a separation step applied to such materials. It should also be appreciated that, while blood products are specifically cited, such methods are applicable to any solution containing a protein of interest (e.g., cell culture media, lysates of cells from cell culture, bacterial lysates, solvated inclusion bodies, etc.). In the process depicted in FIG. 1 a precipitate from a fractionation process is dissolved prior to application to ion exchange media.

In some embodiments such re-dissolved materials can be clarified, for example by passage through one or more filters, in order to remove residual undissolved or precipitated materials that would foul the chromatography media. In some embodiments the buffer composition of such re-dissolved precipitate can be modified prior to application to the ion exchange media. This can be accomplished through buffer exchange (i.e., a process where salt is removed from the protein containing solution), such as through size exclusion chromatography, dialysis, diafiltration, and/or re-precipitation (e.g., using PEG) followed by re-dissolution. Alternatively, in some embodiments such a re-dissolved precipitate can be diluted (which retains salts originally present in the re-dissolved precipitate) until a desired osmolarity and/or conductivity (e.g., 2 to 10 mS) is achieved. The flow-through fraction from a first ion exchange step is transferred to a second ion exchange step utilizing an ion exchange media with similar charge characteristics (i.e. anion exchange, cation exchange), and the protein of interest is recovered in the flow-through fraction of this second ion exchange step at high yield (e.g., greater than 70%, 75%, 80%, 85%, 90%, or 95% relative to content of the protein of interest in the starting material) and at high purity (e.g., greater that 80%, 85%, 90%, 95%. 98%, or 99%). Inventors contemplate that in some embodiments a single large ion exchange column can be used in place of two ion exchange columns, however such an approach would necessarily limit the scale of operations. Although the ion exchange steps are shown as anion exchange steps, embodiments in which the ion exchange steps are performed using a cation exchange media are also contemplated and can be applied to isolation of proteins other than IgG.

Figure 2:
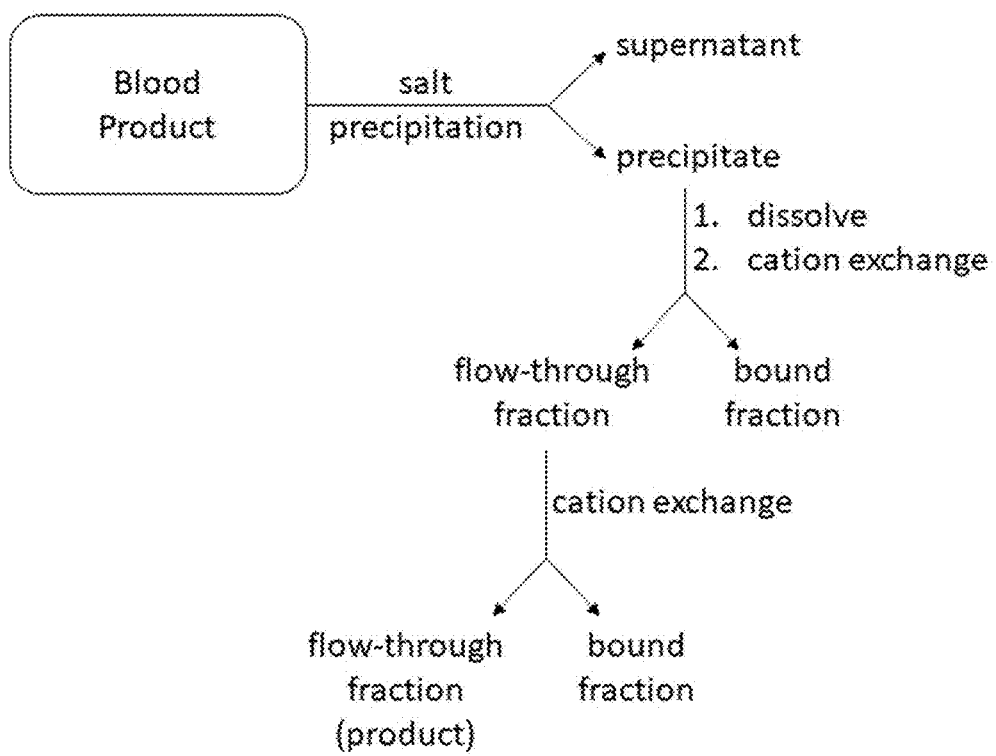
FIG. 2 schematically depicts an exemplary process of the inventive concept utilizing two anion exchange steps in succession.

Another embodiment of the inventive concept is shown in FIG. 2, in which the initial ion exchange step is performed on a supernatant derived from the fractionations step. In some embodiments such a supernatant can be clarified, for example by passage through one or more filters, in order to remove residual particulate or precipitated materials that would foul the chromatography media. In some embodiments the buffer composition of such a supernatant can be modified prior to application to the ion exchange media. This can be accomplished through buffer exchange (i.e., a process where salt is removed from the protein containing solution), such as through size exclusion chromatography, dialysis, diafiltration, and/or precipitation (e.g., using PEG) followed by dissolution. Alternatively, in some embodiments such supernatant can be diluted (which retains salts originally present in the supernatant) until a desired osmolarity and/or conductivity (e.g., 2 to 10 mS) is achieved. The flow-through fraction from a first ion exchange step is transferred to a second ion exchange step utilizing an ion exchange media with similar charge characteristics (i.e. anion exchange, cation exchange), and the protein of interest is recovered in the flow-through fraction of this second ion exchange step at high yield (e.g., greater than 70%, 75%, 80%, 85%, 90%, or 95% relative to content of the protein of interest in the starting material) and at high purity (e.g., greater that 80%, 85%, 90%, 95%. 98%, or 99%).

It should also be appreciated that, while blood products are specifically cited in FIGS. 1 and 2, such methods are applicable to any solution containing a protein of interest (e.g., cell culture media, lysates of cells from cell culture, bacterial lysates, solvated inclusion bodies, etc.). Although the ion exchange steps are shown as anion exchange steps, embodiments in which the ion exchange steps are performed using a cation exchange media are also contemplated. Such methods can, for example, be used in the isolation of proteins other than IgG.

Figure 3:
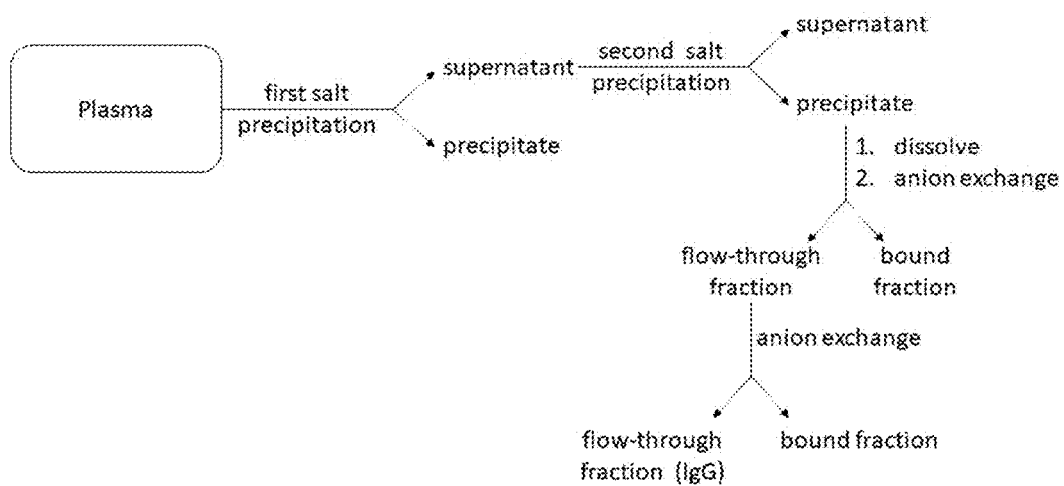
FIG. 3 schematically depicts an exemplary process of the inventive concept as applied to isolation of immunoglobulin G (IgG) from a blood product using two anion exchange steps in succession.

Inventors have found methods of the inventive concept are particularly useful in the isolation of IgG from blood plasma, although application to other solutions containing IgG (e.g., cell culture media, cell lysates, dissolved inclusion bodies, other body fluids, etc.) is contemplated. Within the context of this application plasma is considered to include freshly collected serum, freshly collected plasma, reconstituted lyophilized plasma, refrigerated plasma, frozen plasma, recovered plasma, cryo-poor plasma, cryo-poor plasma into which the cryoprecipitate has been re-dissolved, and mixtures of two or more of these. Such plasma can, for example, be obtained as pooled material from a blood or plasma collection center. An example of a method of the inventive concept for isolation of IgG from plasma is shown in FIG. 3.

For the first two steps the Inventors modified and/or optimized a base fractionation process using a range of salt concentrations for two precipitation steps to determine the optimum concentrations (e.g., about 11% in the first salt precipitation and about 26% in the second salt precipitation) and to maximize IgG yield while minimizing unwanted proteins. While citrate or acetate salts are preferred, any suitable salt can be used. Such salts can be added rapidly, as a salt solution (e.g., as a calculated volume of a 50% by weight salt solution) and/or in dry form (e.g., as a powder or crystalline solid). As shown the first precipitation step produces an IgG-rich supernatant, and the second precipitation step produces an IgG-rich precipitate or paste. This IgG-rich precipitate is dissolved (e.g., in water) prior to ion exchange steps. In such embodiments a buffer exchange step (e.g., dialysis, diafiltration, ultrafiltration followed by dilution, size exclusion chromatography, etc.) can be performed prior to ion exchange steps. Alternatively, the re-dissolved precipitate can be diluted until a desired conductivity (e.g., 2 to 10 mS) or ionic strength is achieved. It should be appreciated that precipitation can occur during buffer exchange steps, and that additional filtration steps (e.g., depth filtration, or depth filtration followed by a clarifying or polishing filtration step) can be implemented to remove such precipitated materials prior to the initial ion exchange step. As shown in FIG. 3, in an at-scale IgG process of the inventive concept IgG can be recovered in the flow-through (i.e., unbound) fraction from the second anion exchange step.

In some embodiments a virus inactivation step is applied to the dissolved IgG-rich precipitate prior to an ion exchange step. For example, the pH can be lowered to 5.7 and caprylate added to inactivate enveloped viruses. Such steps do not appear to contribute to any significant IgG losses and caprylate can be effectively removed in subsequent ion exchange steps.

In conventional protein purification processes yield is sacrificed for purity of the final protein product. Surprisingly, in the methods described herein IgG is typically recovered at both high yield (greater than 70%, 75%, 80%, 85%, 90%, or 95% of the IgG present in the starting material) and high purity (greater than 80%, 85%, 90%, 95%, 98%, or 99%).

EXAMPLES

Multiple base fractionations of IgG from cryo-precipitate poor plasma in two precipitation steps utilizing sodium citrate as the precipitant were performed. Two-liter test batches were prepared in pilot facilities. The IgG yield achieved was 90% in the second precipitate (i.e., precipitate resulting from the second precipitation step) and with only 3% in the second supernatant (i.e., supernatant resulting from the second precipitation step), while the second achieved 95% yield in the second precipitate and only 3% in the second supernatant. The uniform presence of ~3% IgG in second supernatant indicates that the base fractionation process is robust and yields approximately 95% of the starting IgG in plasma.

A range of sodium citrate concentrations were explored to develop an optimal protocol for IgG yield and purity through the base fractionation process. Cryo-poor plasma was subjected to an initial 11% sodium citrate (w/v) precipitation step for 1 hour followed by centrifugation at 4,500×g. The resulting first supernatant 1 was further fractionated in a second sodium citrate precipitation step for 2 hours at citrate concentrations ranging from 22% to 28% (w/v) sodium citrate followed by centrifugation at 4,500×g. Pastes from the first precipitation steps (i.e., first precipitates) and second precipitation steps (i.e., second precipitates) were dissolved in water for injection at a concentration of 10 mL water per gram of wet paste. During fractionation processes both temperature (2-8° C.) and pH (7.0±0.1) were maintained. Citrate concentration was adjusted by adding 50% w/v sodium citrate at ambient temperature (20-25° C.).

Analysis of total protein and IgG content was carried out largely by $A_{280}$ measurement and total IgG ELISA (Invitrogen), respectively. While the total IgG ELISA's measurement precision can be less accurate in complex solutions, such as cryo-poor plasma, it is suitable method for measuring relative IgG concentrations in process steps with increasingly pure IgG.

Typically, a 98% recovery of IgG in the first supernatant was found in the initial 11% (w/v) citrate precipitation step (data not shown). As shown in Table 1, IgG yield in the second precipitate from the second precipitation step increases as citrate concentrations increase from 22% to 24% (w/v), then plateaus at citrate concentrations of from 26% and 28% w/v (at about 85% IgG recovery from the first supernatant). These data are further corroborated by the IgG concentrations observed in the corresponding second supernatants, which display the inverse trend.

TABLE 1

| Sample | $2^{nd}$ Precipitate weight (g) | IgG Recovery (%) |
| --- | --- | --- |
| 22% Sup | N/A | 29 |
| 22% Paste | 19.7 | 68 |
| 24% Sup | N/A | 13 |
| 24% Paste | 27.7 | 71 |
| 26% Sup | N/A | 9 |
| 26% Paste | 33 | 85 |
| 28% Sup | N/A | 11 |
| 28% Paste | 39.8 | 85 |

Figure 4:
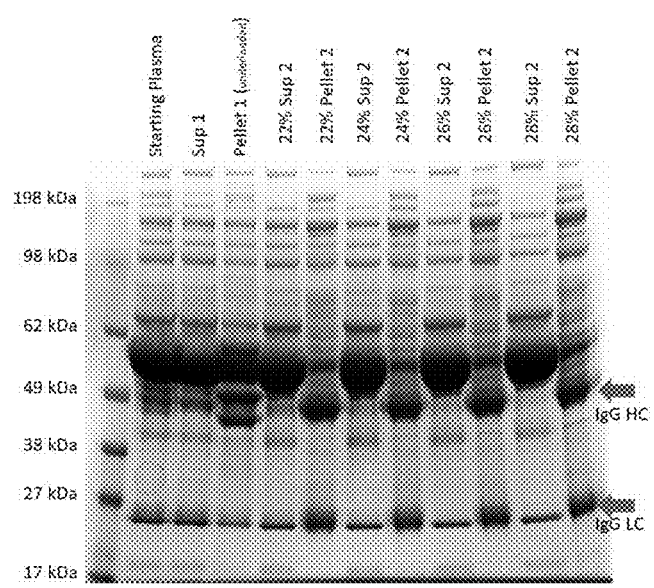
FIG. 4 shows results of SDS-PAGE performed on supernatants and precipitates generated during a second precipitation step at different citrate concentrations, under reducing conditions. The arrows denote the heavy (HC) and Light chains (LC) of IgG under reducing conditions.

The increase in second precipitate weight without corresponding increases in IgG yield indicates that precipitation beyond 26% (w/v) citrate accumulates undesired contaminating proteins. This was confirmed by SDS-PAGE (FIG. 4). FIG. 4 shows results from a 4-12% SDS-PAGE gel run under reducing conditions of the fractionation process applied to cryo-poor plasma. Arrows denote the heavy (HC) and light chains (LC) of IgG. The gel was loaded with 20 $A_{280}$ units of protein per lane. As shown, IgG is evident in the first supernatants (S1) and second precipitates (Pellet 2), with increasing protein contamination observed in the second precipitate at high (e.g., 26%, 28% w/v) citrate concentrations in the second precipitation step.

Figure 5:
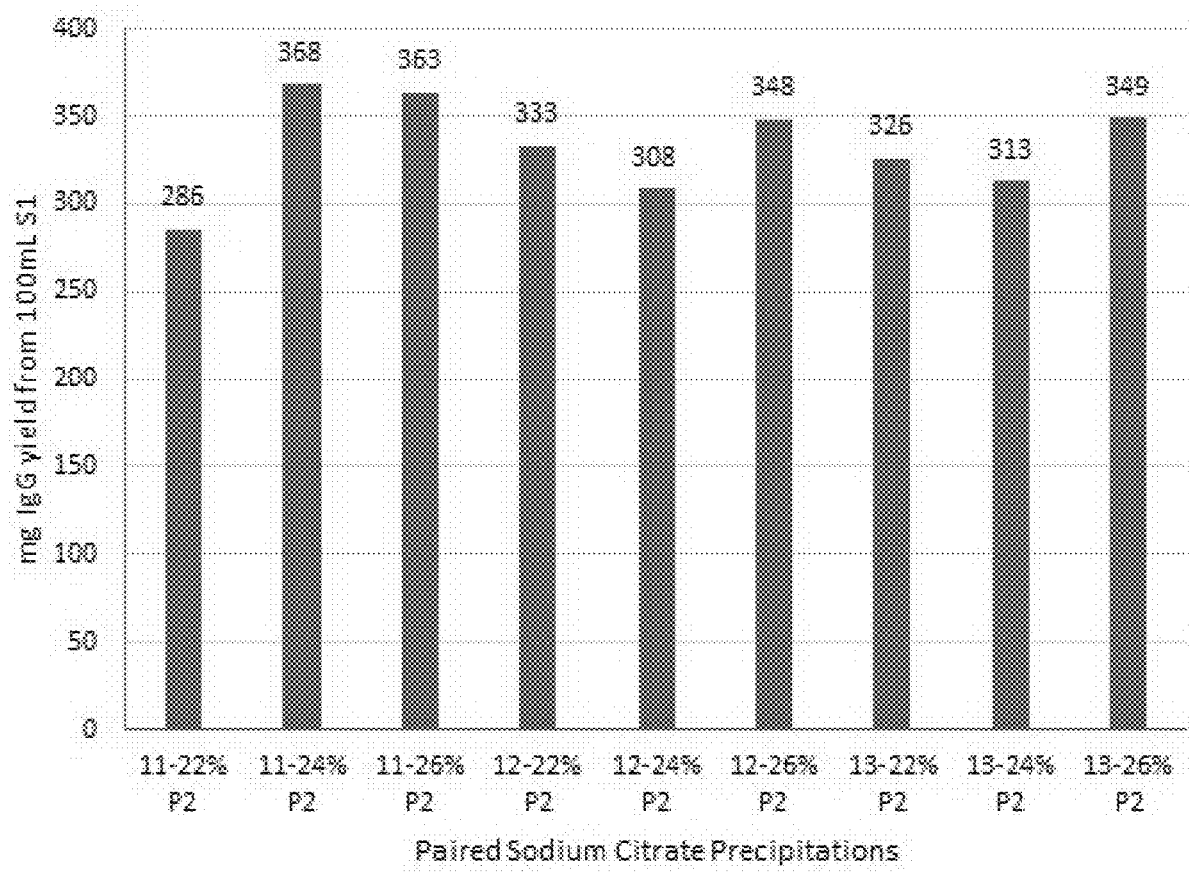
FIG. 5 shows results of IgG precipitation studies and mean (N=3) second precipitate IgG recoveries.

Robustness of the precipitation steps was characterized by fractionating aliquots of the same cryo-poor plasma pool with 11-13% (w/v) citrate and then with 22-26% citrate (w/v). IgG yields in the resulting supernatants and precipitates were analyzed via ELISA. The mean IgG levels obtained are shown in FIG. 5. FIG. 5 provides a histogram of mean results obtained with different pairs of first precipitation and second precipitation citrate concentrations (e.g., "11-22%" indicates 11% w/v citrate in the first precipitation step and 22% w/v citrate in the second precipitation step). As shown, 11% citrate (w/v) in the first precipitation step and 24% to 26% (w/v) citrate in the second precipitation step 11-24% were optimal to achieve maximum IgG yields. Initial precipitation at 12 or 13% (w/v) citrate appeared to have comparably lower IgG yields when the second precipitation step was conducted at varying concentrations.

To further characterize robustness of initial precipitation steps, four 2 L volumes of a pooled cryo-poor plasma were processed, each using an 11% (w/v) citrate concentration for the initial precipitation and a 26% (w/v) citrate concentration for the second precipitation step. The second precipitate from each of these was dissolved in water for injection (10 mL/g of wet paste). IgG concentrations were measured by nephelometry. Results are shown in Table 2.

TABLE 2

| Sample | Batch A Yield (%) | Batch B Yield (%) | Batch C Yield (%) | Batch D Yield (%) | Mean Yield (%) |
| --- | --- | --- | --- | --- | --- |
| Cryo-poor plasma | 100.0 | 100.0 | 100.0 | 100.0 | 100.0 |
| $1^{st}$ Supernatant | 97.3 | 99.5 | 98.5 | 97.0 | 98.1 |
| $1^{st}$ Precipitate | 0.6 | 0.7 | 0.5 | 0.9 | 0.7 |
| $2^{nd}$ Supernatant | 6.1 | 7.5 | 5.2 | 6.0 | 6.2 |
| $2^{nd}$ Precipitate | 90.2 | 89.9 | 91.0 | 90.2 | 90.3 |

As shown, the nephelometry data are very consistent and show a 98.1% mean recovery of IgG in the first supernatant obtained from the starting cryo-poor plasma after the initial 11% precipitation step. This data is consistent with the lack of IgG (<1%) in the first precipitate. The final IgG yield in the second precipitate across the four batches in P2 was 90.3% IgG and mean value of 6.2% IgG remaining in the second supernatant. Inventors believe that some IgG-containing precipitate was not collected during centrifugation, and that recovery of IgG in the second precipitate can be about 95% or greater in the second precipitate with more extensive centrifugation.

It was noted that on dissolving such second precipitates in water for injection at 10 mL/g wet paste, the solution can appear cloudy and/or opalescent. Inventors believe that cloudiness is likely the result of suspended lipids and non-solubilized impurities. In small-scale studies dialysis was used for buffer exchange (i.e., removal of salts from the IgG-containing solution) prior to subsequent ion exchange steps. Such precipitated materials can be removed by centrifugation or filtration (e.g., using a depth filter) prior to application of the dialyzed material to ion exchange media in order to avoid fouling. Similar precipitation was noted during the use of diafiltration which made diafiltration unsuitable for buffer exchange prior to ion exchange chromatography.

The Inventors found that on scale-up, when depth filtration was used to remove materials precipitating from the re-dissolved second precipitation it was found that additional non-IgG proteins were being introduced into ion exchange chromatography. At a small scale such non-IgG proteins were removed in the dialysis/centrifugation process and did not contribute to the protein burden on the ion exchange column.

In anion exchange media capacity studies, breakthrough on a Q-Sepharose™ column was determined to occur at approximately 14 $A_{280}$ units per mL of resin. After 2 injections of 35 $A_{280}$ units (14 $A_{280}$/mL) onto a 5 mL Q-Sepharose™ column high molecular weight contaminants begin to appear in several places above the 62 kDa marker with significant albumin (·60 kDa) breakthrough occurring after a third 35 $A_{280}$ unit injection (21 $A_{280}$/mL). Typical results of such studies are shown in an SDS-PAGE gel in FIG. 6.

Figure 6:
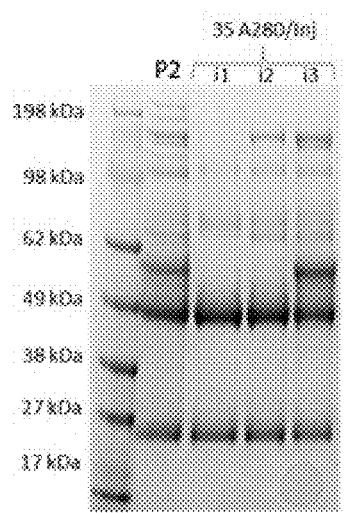
FIG. 6 shows typical results of bis-tris SDS-PAGE of samples obtained from Q-Sepharose™ column breakthrough studies.

FIG. 6 shows a reduced bis-tris SDS-PAGE page gel of samples obtained from Q-Sepharose™ column breakthrough studies. A 5 mL Q-Sepharose™ column was successively loaded with 3 injections of 35 $A_{280}$ of P2 material that had been passed through the DL10 depth filters and XLG filters, respectively. Lane 1 contains molecular weight standards. Lane 2 contains filtered second precipitate. Lane 3 contains flow-through fraction following injection 1 (as described above). Lane 4 contains flow-through fraction following injection 2. Lane 5 contains the flow-through fraction following injection 3. The mean±SD protein load across three batches of depth-filtered dissolved second precipitate was 23,162±2,000 $A_{280}$ units. This equates to a Q-Sepharose column size of at least about 1 L/1 L of starting plasma to satisfy the upper standard deviation and a 10% safety margin.

Typically, isolation of IgG using ion exchange chromatography utilizes anion exchange as negative selection (i.e., the IgG is not bound) coupled to cation exchange as a positive selector to which IgG is bound and subsequently eluted after contaminants are washed from the bound IgG. Such binding, washing, and elution steps in cation exchange chromatography limit scalability of such approaches and also provide additional opportunities for loss of IgG during the process.

Figure 7:
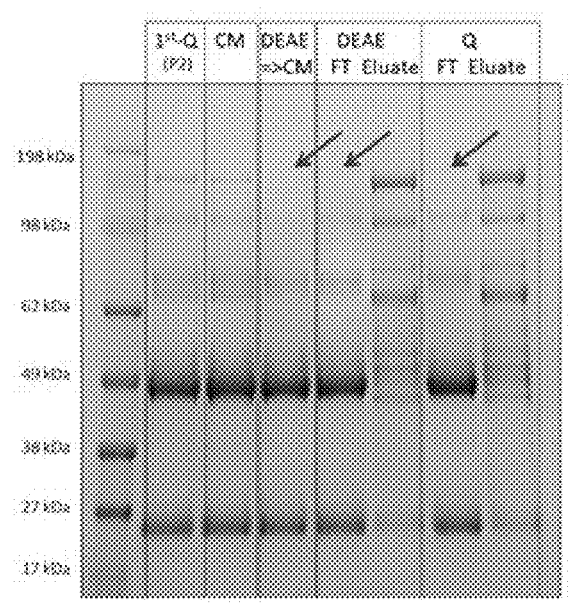
FIG. 7 shows results of reduced bis-Tris SDS-PAGE of samples obtained from different ion exchange column arrangements. IgG product derived from various ion exchange chromatography column arrangements.

Inventors used information regarding Q-Sepharose™ column capacity as shown in FIG. 6 to develop a different chromatography framework. Dissolved and depth-filtered second precipitate material was initially processed over a Q-Sepharose™ (an anion exchanger) column (14 $A_{280}$/mL) to generate a pool of material that was applied to different downstream chromatography schemes. An amount of such pooled material representative of flow-through from a single 5 mL Q-Sepharose™ column run was subsequently applied to each of a second 5 mL Q-Sepharose™ column, a 5 mL DEAE Sepharose™ column, a 5 mL CM-Sepharose™ column, or a 5 mL DEAE Sepharose™ column coupled to a 5 mL CM Sepharose™ column. In the case of the coupled DEAE/CM columns, the DEAE Sepharose™ column was uncoupled from the CM Sepharose™ column prior to elution of the CM Sepharose™ column. FIG. 7 provides a bis-Tris SDS-PAGE page gel of IgG products derived from various chromatography column schemes. Lane 1 contains a molecular weight standard. Lane 2 contains the initial flow through from a single Q-Sepharose™ column. Lane 3 contains eluate from a CM Sepharose™ column. Lane contains material resulting from applying flow-through from a DEAE Sepharose™ column and eluate obtained from applying this flow-through to a CM Sepharose™ column. Lane 5 contains flow-through from a DEAE Sepharose™ column. Lane 6 contains eluate from a DEAE Sepharose™ column. Lane 7 contains flow through from a second Q-Sepharose column. Lane 8 contains eluate from the second Q-Sepharose™ column. Arrows indicate resin combinations that removed a high molecular weight component, thus producing a higher-purity product.

Materials indicated by arrows in FIG. 7 were analyzed by LCMS to determine the relative IgG purity produced in each column scheme. The products of all column arrangements appear to have similar purities.

Three complete runs were performed using cryo-poor plasma at a 2 L scale and two similarly sized 2 L Q-Sepharose™ columns arranged in succession. Chromatography was performed on an AKTA Explorer FPLC™ system. The final conditions for these processes were as follows: 2×2 L Q-Sepharose™ columns (1× Axichrome™ 100/300 and 1× Axichrome™ 140/300) coupled in sequence and equilibrated in 20 mM NaOAC pH 5.7. The columns were loaded at 45 mL/min, washed at 50 mL/min and eluted with a 2M NaCl step (implemented at 9500 mL). One-liter fractions were collected based on $A_{280}$ reading. Under these conditions, a high-purity IgG with acceptable FXIa levels was obtained, indicating that the process is scalable. The physical characteristics of the three batches (batches D, E, and F) after filtration are shown below in Table 3.

TABLE 3

| Batch # | Volume (mL) | A280 | Total A280s | Conductivity |
|---|---|---|---|---|
| E | 3923 | 5.9 | 23067 | 7.01 |
| F | 4127 | 5.2 | 21254 | 6.86 |
| G | 4146 | 6.1 | 25166 | 7.12 |
| Mean | 4065 | 5.7 | 23163 | 7.0 |

Figure 8:
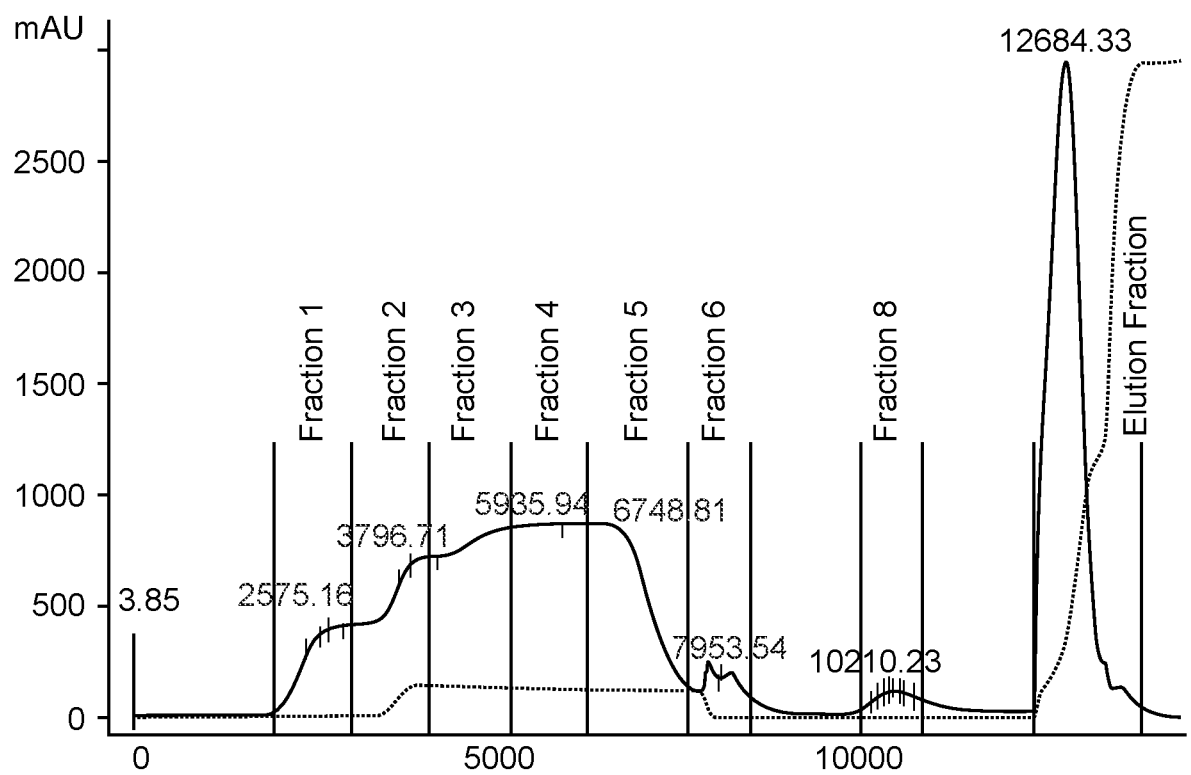
FIG. 8 shows typical A280 measurement obtained during chromatography of a 2 L pilot scale method performed on successive 2 L Q-Sepharose™ columns. Individual fractions are denoted by vertical lines.

In general, all 2 L scale processes performed identically in chromatography with no significant differences between profile or fraction collection. For illustrative purposes batch E was chosen as representative example. Fraction collection for product was started when the $A_{280}$ reached 50 mAU and terminated when the absorbance decreased to 125 mAU. As shown in FIG. 8, the primary flow-through peak (Fractions 1-5) was, surprisingly, not uniform in shape and contained 3-4 distinct features topping off at a maximum $A_{280}$ of 900 mAU/mL. Two smaller features (Fractions 6, biphasic peak and Fraction 8 single peak) were observed after the main peak. The elution peak (Elution fraction) is primarily uniform in shape with a complex tail of material. In the chromatogram shown in FIG. 8 individual fractions are indicated by vertical bars.

Figure 9:
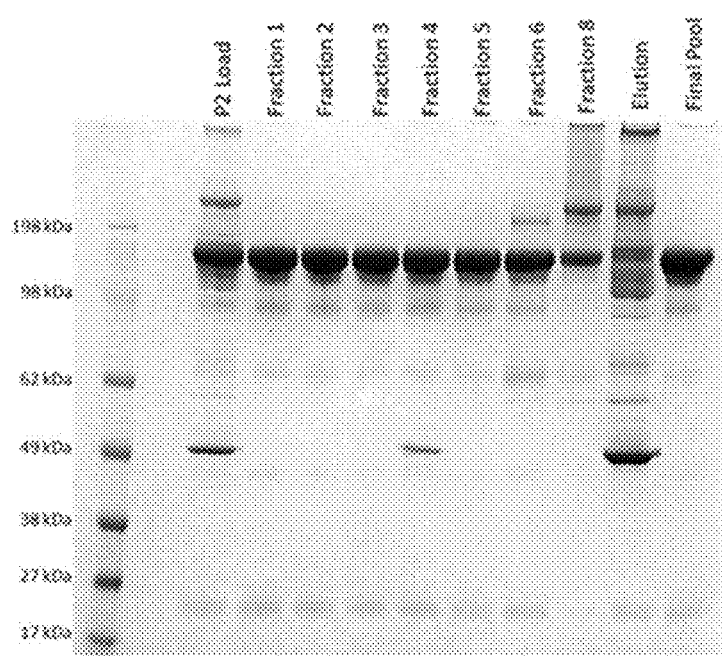
FIG. 9 shows typical results of non-reduced bis-tris SDS-PAGE of samples obtained during chromatography of a 2 L scale process of the inventive concept. Lane labels correspond to the labeled fractions in FIG. 8. The "final pool" consists of fractions 1 to 5.

FIG. 9 shows results of non-reduced bis-tris SDS-PAGE on a gel loaded with 10 $A_{280}$ units per lane of respective fractions collected from batch E Q-Sepharose™/Q-Sepharose™ chromatography. Lane labels correspond to the labeled fractions in FIG. 8. The "final pool" consists of a pool of fractions 1 to 5, each of which appears to be pure IgG (150 kDa) with a slight extra band (~200 kDa) visible in fraction 5. This band is apparently a "bleed through" from the biphasic peak of material contained in fraction 6 and appears to consist of a ~200 kDa protein species mixed with an IgG species. The final pool (fractions 1 to 5) appears to be >95% IgG with no obvious contaminants present.

Regulatory requirements can necessitate that two virus inactivation/removal steps be included in any biological processing of human-derived products manufactured for human use. To that end, methods of the inventive concept can include a virus inactivation step applied to the second precipitate, and/or nano filtration to remove viruses after ion exchange chromatography.

Two-liter scale methods can be modified to incorporate, for example, treatment with 20 mM sodium caprylate for 1 hour at room temperature for viral inactivation prior to depth filtration. A small amount of white precipitate can be formed upon addition of caprylate to the dissolved second precipitate. Table 4 shows the caprylate content of samples from treatment through Q-Sepharose™ chromatography. After Sartoclear™ DL10 depth filtration 63% of the original bolus of caprylate is detectable in the clarified sample. When dilution of P2 post depth filtration sample is accounted for in the post Sartoclear™ XLG sterilization filter sample there is no loss of caprylate in this filtration step. All remaining caprylate is removed during Q-Sepharose™ chromatography with no detectable levels of caprylate observed in any IgG fraction after this process step.

TABLE 4

| Sample | Caprylate (mM) |
|---|---|
| Post DL10 | 12.6 |
| Post XLG | 6.4 |
| Post Q-Sepharose | N/D |

In addition to virus inactivation, virus removal (e.g., by nanofiltration) can be applied for virus removal. For example, nanofiltration can be applied as the second of two virus inactivation/removal steps in methods of the inventive concept. Virus removal can be accomplished using any suitable nanofilter/nanofiltration device and/or method. Suitable nanofiltration devices include, but are not limited to, a Sartorius Virosart Max™ 0.1 μm prefilter followed by a Sartorius Virosart HC™ 0.02 μm virus removal filter. In a typical virus removal step a prefilter and virus removal filter are attached in sequence and flushed with water per manufacturer's instructions prior to addition of the product material. For example, a coupled set of 220 cm² Virosart Max™ and Virosart HC™ filters (Sartorius) can be used for processing material derived from about 2 L of plasma. Alternatively, two or more coupled sets of such coupled filters can be used to, decrease loss of flux through the filter assembly and decrease processing time.

Use of flow-through fractions throughout methods of the inventive concept for isolation of a protein of interest can yield solutions in which the concentration of the target protein is non-optimal for clinical application. Accordingly, methods of the inventive concept can include a terminal protein concentration step that takes place after the protein of interest has been purified and utilizes techniques known in the art. Such concentration steps can, for example, be performed by ultrafiltration, and can incorporate a diafiltration step that permits buffer exchange into a pharmaceutically acceptable buffer composition. For example, in the isolation of IgG the highly purified product material can be concentration to about 4% (w/v) or higher (e.g., about 5% w/v) IgG, with diafiltration during the concentration step used to replace the extant buffer with 0.2M Glycine (pH 4.2 to 6.5) or any other pharmaceutically acceptable buffer. For example, such a concentration/diafiltration step can be performed in three steps: (1) concentration of a nanofiltered protein solution to a volume approximately 500 mL, (2) diafiltration of the approximately 500 mL volume into a formulation buffer (e.g., 8 or more diavolumes), and (3) concentration of the diafiltered volume to the target concentration of protein (e.g., about 5% w/v IgG). Protein concentration can, for example, be monitored by absorbance at 280 nm.

The overall IgG yield of the three batches (E, F, G) was determined using a validated nephelometric assay for the starting plasma as well as for the subsequent fractions of the precipitation steps. Once the purification efforts had reached purities of over 90% IgG, $A_{280}$ measurement and an extinction coefficient of 1.3 were used to quantify IgG. Table 5 shows the mean total IgG for all three batches present at each process step. The mean process yield is 75% with the most significant process losses occurring in the depth filtration (~8%) and Q-Sepharose™ chromatography (~9%) steps.

TABLE 5

| Sample | Protein Concentration Nephelometry (g) | Protein Concentration $A_{280}$ (g) | Mean Yield (%) |
|---|---|---|---|
| Cryo-Poor Plasma | 16.1 | | 100 |
| 1$^{st}$ Supernatant | 15.8 | | 95 |
| 2$^{nd}$ Precipitate | 14.5 | | 88 |
| Post Depth filter | 13.2 | | 80 |
| Post Clarification filter | 12.7 | | 79 |
| Second Q-Sepharose Flow-Through | | 11.2 | 70 |
| Post-Nanofiltration | | 11.0 | 68 |
| Final | | 12.1 | 75 |

The chromatography step performed using two anion exchange columns arranged in series removes >99% of all proteins other than IgG. Surprisingly, it was found that two small trailing peaks (fractions 6 and 8 in FIG. 8) of material contain IgG species and contain no measurable IgA or IgM (by ELISA). IgG species in both of these fractions are disproportionately (~30%) IgG4. Inventors believe that the atypical shape of the Q-Sepharose™ chromatography flow-through fraction is due to differential, transient retention of the four IgG subclasses found in the sample inputted to the columns. IgG subclass ELISA data indicates that IgG1 continuously appears throughout the flow-through fraction, the second shoulder (fraction 3 on FIG. 10) appears to be enriched in types 2 and 3 while IgG4 predominantly elutes towards the end of the main UV 'peak' (fraction 5). This unexpected result could be a function of limited IgG interaction the anion exchange resin at the buffer conductivity used (about 7 mS), thereby essentially retarding progress of some IgG subclasses through the column without binding. Inventors believe that buffer conditions and anion exchange media selection and/or capacity can be optimized to provide IgG subclass separation in a flow-through fraction from anion exchange chromatography, in an integrated process starting with a blood product.

In prior art process for protein isolation there is generally an inverse relationship between yield and purity of the protein product. Surprisingly, Inventors have found that methods of the inventive concept can provide both very high yields (in excess of 70% of IgG content of starting material) and high purity. Comprehensive analytical testing was performed to examine the safety and co-purifying non-IgG protein content for several IgG product purifications using a method of the inventive concept employing two Q-Sepharose™ columns arranged in series, with IgG collected in flow-through fractions.

Figure 10:
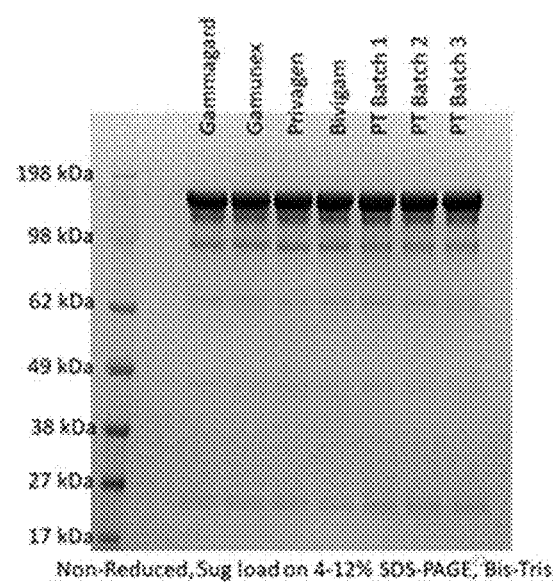
FIG. 10 shows typical results of non-reduced bis-tris SDS-PAGE of four commercially available intravenous IgG products and final product from three 2 L scale batches produced by a method of the inventive concept. 5 µg protein were loaded per lane.

As shown in FIG. 10, SDS-PAGE indicates a product purity of >98% IgG, matching or exceeding that of current commercial IgG products for human use. Specifically, when examined in comparison to commercially available intravenous IgG products (Gammagard™, Gamunex™ Privagen™, and Bivigam™), the final product IgG has fewer HMW contaminants.

Analytical testing results of IgG products from a method of the inventive concept employing two Q-Sepharose™ are shown in Table 6. For this purpose, IgG products from 2 L scale batches produced using such a method of the inventive concept were formulated in 0.2M Glycine pH 4.2, with a target of about 5% total protein. This is consistent with current practice in regard to therapeutic IgG products for human use. IgG concentrations were determined by absorbance at 280 nm by spectrophotometry. Additional protein content determinations were performed on the final product formulations. The mean concentrations across methods (N=5) of the three respective final formulations were 41.2, 52.9 and 50.9 mg/mL, respectively. IgG Subclass distribution was measured by IgG subclass ELISA and determined to be 63% IgG1, 28% IgG2, 7% IgG3 and 2% IgG4 across the three final formulations. The respective cryo-poor plasma starting material values were 59% IgG1, 29% IgG2, 7% IgG3, and 4% IgG4. In regard to other immunoglobulin species, only IgA was detected by ELISA (3.3 µg/mL) and was confirmed by LCMS. IgA content, however, is below 4 µg/mL. IgM was not detected by ELISA, and LCMS only detected trace amounts of IgM, IgE and IgD peptides mers, and almost undetectable levels of Ig fragments. This meets both FDA and EU specifications for IgG products for human use.

PKA and ACA Activity: PKA and ACA activity are tests for the presence of contaminants that can lead to activation/inactivation of innate immunity through their respective proteolytic cascades. PKA activity was low (Mean=1.3 IU/mL) and well below the 35 IU/mL acceptance criteria typical for IgG products for human use. However, ACA activity was above the 1.0 CH50 U/mg.

Procoagulant Activity: Clotting time measures inherent procoagulant activity (regardless of source), whereas the TGA assay measures FXIa-like activity. At the lowest dilution, batch E (141 sec) barely failed to meet the >150 sec acceptance criteria, while batches F and G passed. FXIa-like activity in all three batches was somewhat high (>2.0 mU/mL) indicating activation of the contact pathway of coagulation at some point

TABLE 6

| Test Method | | Batch E | Batch F | Batch G | Acceptance Criteria |
|---|---|---|---|---|---|
| SDS-PAGE Purity | | 98% | 98% | 98% | ≥96% |
| Purity by LCMS (Std. Dig.) | | 99.2 | 99.3 | 99.3 | No ACC |
| IgG by Spectrophotometry | | 41.9 mg/mL | 54.0 mg/mL | 48.4 mg/mL | No ACC |
| Protein by Bradford Assay | | 43.9 mg/mL | 53.5 mg/mL | 54.6 mg/mL | No ACC |
| IgG Nephelometry | | 37.2 mg/mL | 48.9 mg/mL | 47.0 mg/mL | No ACC |
| Total IgG ELISA | | 36.2 mg/mL | 47.7 mg/mL | 48.3 mg/mL | No ACC |
| IgG Protein G HPLC | | 46.6 mg/mL | 60.5 mg/mL | 56.4 mg/mL | No ACC |
| IgG Subclass | IgG 1   IgG 2 | 63%   28% | 63%   28% | 62%   28% | Starting Plasma |
| Distribution | IgG 3   IgG 4 | 7%   2% | 7%   2% | 7%   2% | IgG 1  IgG 2  IgG 3  IgG 4<br>59%   29%    7%     4% |
| IgA | | 2.9 µg/mL | 3.6 µg/mL | 3.4 µg/mL | As stated on label |
| IgM | | ND | ND | ND | <1 µg/mL |
| Caprylate | | ND | ND | ND | No ACC |
| TGA (mU/mL) | | All values >2.0 mU/mL | | | ≤1.0 mU/mL |
| Anti-A Titer Value | | 32 | 32 | 32 | ≤64 |
| Anti-B Titer Value | | 16 | 16 | 16 | ≤64 |
| Anti-D Titer Value | | No titer | No titer | No titer | ≤8 |
| Anti-Complement (CH$_{50}$ U/mg IgG) | | All values >1.0 CH$_{50}$ U/mg | | | ≤1.0 CH$_{50}$ U/mg |
| Fc | 15 mg IGIV | 136% | 100% | 129% | ≥60% |
| Function | 30 mg IGIV | 100% | 114% | 110% | ≥60% |
| PKA (IU/mL) | | 1.0 | 1.7 | 1.3 | ≤35 IU/mL |
| NAPTT Clot Time | | 141 s | 177 s | 220 s | ≥150 s |
| SE-HPLC | % Dimer | 3.884 | 3.722 | 3.794 | Mono-&di-meric ≥90% |
| | % Monomer | 95.911 | 96.143 | 96.055 | Polymeric <2% |
| | % IGIV | 99.795 | 99.866 | 99.849 | Fragment <3% |
| | % Polymeric (HMW) | 0.027 | 0.012 | 0.021 | |
| | % Fragment (LMW) | 0.179 | 0.123 | 0.130 | |

Product from an IgG isolation method of the inventive concept employing two anion exchange columns arranged in series was characterized for content related to safety and efficacy. Accordingly, Anti A, B and D antibodies, anti-complement activity (ACA), protein Kinase A (PKA) activity, Fc function, activated coagulation factor XI (FXIa) activity by thrombin generation assay or TGA), and non-activated partial thromboplastin time (NAPTT) activity were characterized for several 2 L scale final product formulations. Results were as follows:

Anti A,B,D Antibodies: All three product batches tested passed typical acceptance criteria for products for human use.

Fc Function/Polymerization: Fc function in all three product batches was >100% at the two concentrations of IgG tested, which meets or exceeds typical acceptance criteria for IgG product for human use. Furthermore, SE-HPLC data indicates that >96% of the IgG is monomeric with <4% dimer, <0.2% higher order polyduring the purification process. In order to eliminate FXIa (i.e., activated factor XI) and other trace contaminations use of a cation exchange column applied to effluent from the serially arranged Q-Sepharose™ columns can be used, by binding IgG found in the Q-Sepharose™ eluate and subsequent elution of IgG from the cation exchange media. While optimizing conditions for this process Inventors surprisingly found that contaminating contact activation factors (e.g., activated Factor XI), as well as other contaminants, bound to the cation exchange media with higher affinity than IgG. This observation was used to scale the capacity of the cation exchange medium to match the amount of the contaminants, thereby preventing binding of IgG to the cation exchange media. With this adjustment, the cation exchange medium can be used in negative selection mode (i.e., with collection of the desired protein product in the flow-through), as shown below.

Alternatively, some embodiments of the inventive concept utilize both anion and cation exchange chromatography, where buffer conditions, differential protein affinity, and binding capacity of ion exchange chromatography media are selected or optimized to provide the target protein (e.g., IgG) in the flow-through fraction of each chromatographic step. Towards this end an initial ion exchange step (e.g., anion exchange, cation exchange) can be performed using a high capacity ion exchange media that does not appreciably bind the protein of interest. For example, in the isolation of IgG a large/high capacity anion exchange step can be performed, providing a flow-through fraction containing IgG and retaining a bound fraction that includes contaminating proteins. The flow-through fraction is then applied (in some embodiments following the addition of a salt to adjust ionic strength/conductivity) to a small or low capacity cation exchange media. It should be appreciated that in conventional processes utilizing both anion and cation exchange, cation media is utilized in the opposite mode of the anion exchange step (where IgG is found in the flow-through fraction). In a conventional IgG isolation process the target protein (IgG) would be retained on the cation exchange media, while the remaining protein contaminations are found in the flow-through fraction. After washing or rinsing the cation exchange media, IgG would then be recovered by elution (e.g., by application of a buffer with high salt content).

In contrast to typical methods, in this embodiment of the inventive concept the cation exchange step is designed to bind the impurities while the protein of interest (IgG) and remains in the flow-through fraction. The size of this small or low capacity cation exchange media is selected so that it is near or slightly (e.g., 1%, 2%, 5%, 10%, 20%, 30%, 40%, 50%) greater than the amount or capacity for breakthrough of a contaminating protein found in the flow-through of the anion exchange media (taking buffer conditions into account). Without wishing to be bound by theory, the Inventors believe that this permits contaminating proteins to displace any IgG that may temporarily bind to the cation exchange media. Careful selection of the amount/capacity of the cation exchange media provides efficient removal of contaminating protein while also providing high yields of IgG in the flow-through fraction.

Another example of a process of the inventive concept is shown below in FIG. 11. It should be appreciated that in this context a blood product can be serum, plasma, refrigerated plasma, frozen plasma, recovered plasma, reconstituted lyophilized plasma, cryo-poor plasma, cryo-poor plasma into which the cryoprecipitate has been re-dissolved, or a fraction a supernatant or a dissolved precipitate) resulting from a precipitation and/or purification step applied to such materials. It should also be appreciated that, while blood products are specifically cited, such methods are applicable to any solution containing a protein of interest (e.g., cell culture media, lysates of cells from cell culture, bacterial lysates, solvated inclusion bodies, etc.). A precipitate produced by salt precipitation (e.g., with a citrate or acetate salt) is re-dissolved and applied to an anion exchange media.

In some embodiments such re-dissolved materials can be clarified, for example by passage through one or more filters, in order to remove residual undissolved or precipitated materials that would foul the chromatography media. In some embodiments the buffer composition of such re-dissolved precipitate can be modified prior to application to the anion exchange media. In some embodiments this can be accomplished through buffer exchange (i.e., a process where salt is removed from the protein containing solution), such as through size exclusion chromatography, dialysis, diafiltration, concentration via ultrafiltration followed by dilution, electrodialysis, and/or re-precipitation (e.g., using PEG) followed by re-dissolution. Alternatively, in preferred embodiments such a re-dissolved precipitate can be diluted (which retains salts originally present in the re-dissolved precipitate) until a desired osmolarity and/or conductivity (e.g., 2 to 10 mS) is achieved. The flow-through fraction from the anion exchange step is transferred to a low capacity cation exchange step using a cation exchange media. In contrast to other processes, the protein of interest is recovered in the flow-through fraction of this second, cation exchange step at high yield (e.g., greater than 70%, 75%, 80%, 85%, 90%, or 95% relative to content of the protein of interest in the starting material) and at high purity (e.g., greater that 80%, 85%, 90%, 95%. 98%, or 99%). The initial ion exchange step is shown as an anion exchange step, however embodiments in which the initial ion exchange step is performed using a high capacity cation exchange media followed by a low capacity anion exchange step (with the protein of interest primarily present in the flow-through volume of both ion exchange steps) are also contemplated, and can be applied to isolation of proteins other than IgG.

Figure 12:
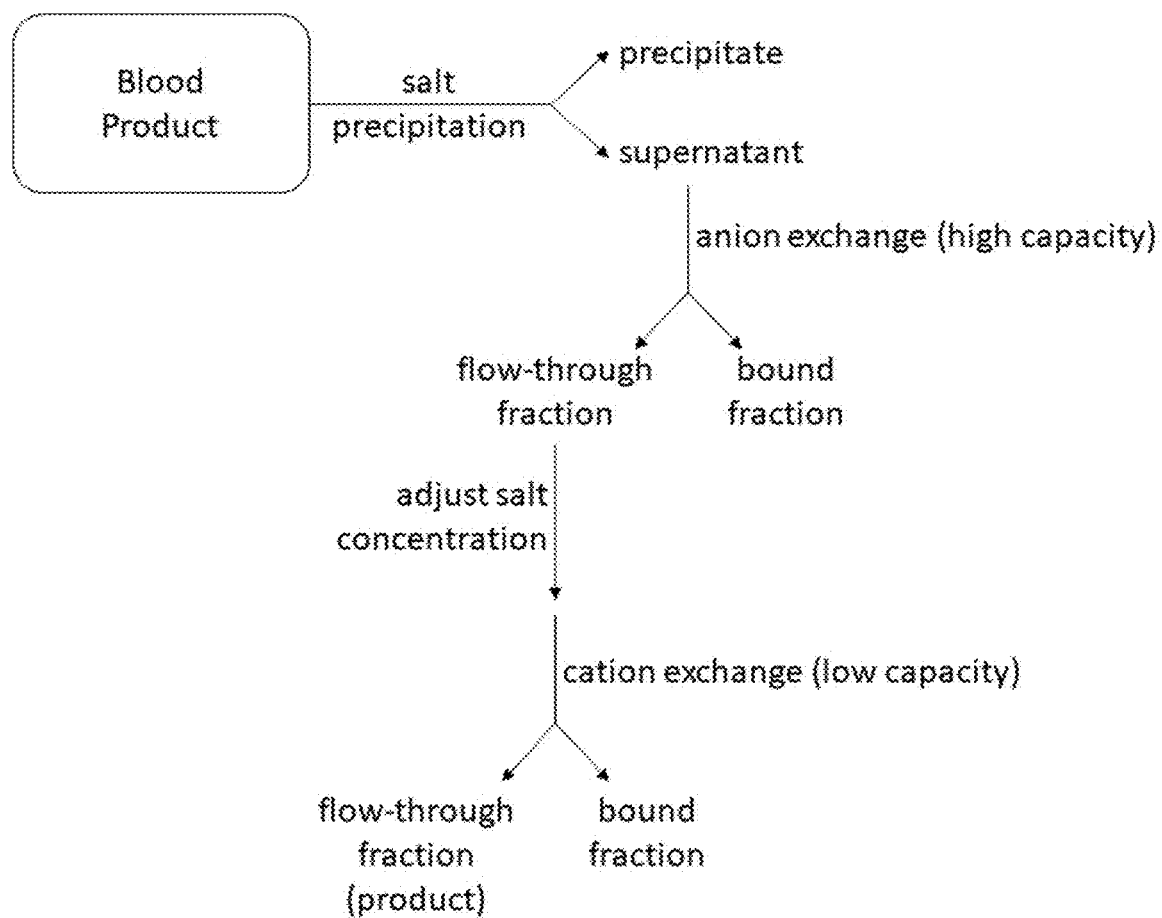
FIG. 12 schematically depicts an exemplary process of the inventive concept utilizing anion exchange and restricted-capacity cation exchange.

Another embodiment of the inventive concept is shown in FIG. 12, in which the initial ion exchange step is performed on a supernatant derived from the fractionations step. It should also be appreciated that, while blood products are specifically cited, such methods are applicable to any solution containing a protein of interest (e.g., cell culture media, lysates of cells from cell culture, bacterial lysates, solvated inclusion bodies, etc.). Although the initial ion exchange step is shown as an anion exchange step, embodiments in which the initial ion exchange step is performed using a high capacity cation exchange media and the second ion exchange step is performed using a low capacity anion exchange media are also contemplated. Such methods can, for example, be used in the isolation of proteins other than IgG.

In some of such embodiments the supernatant obtained from salt fractionation can be clarified, for example by passage through one or more filters, in order to remove residual particulate or precipitated materials that would foul the chromatography media. In some embodiments the buffer composition of such a supernatant can be modified prior to application to the anion exchange media. This can be accomplished through buffer exchange (i.e., a process where salt is removed from the protein containing solution), such as through size exclusion chromatography, dialysis, diafiltration, and/or precipitation (e.g., using PEG) followed by dissolution. Alternatively, in preferred embodiments such supernatant can be diluted (which retains salts originally present in the supernatant) until a desired osmolarity and/or conductivity (e.g., 2 to 10 mS) is achieved. The flow-through fraction from an anion exchange step is transferred to a low capacity cation exchange step utilizing a cation ion exchange media (e.g., a media containing carboxylic acid and/or sulfonate groups). Contrary to prior art processes, the protein of interest is found in the flow-through fraction of the anion exchange step and is recovered in the flow-through fraction of the second, cation ion exchange step at high yield (e.g., greater than 70%, 75%, 80%, 85%, 90%, or 95% relative to content of the protein of interest in the starting material) and at high purity (e.g., greater that 80%, 85%, 90%, 95%. 98%, or 99%).

Figure 11:
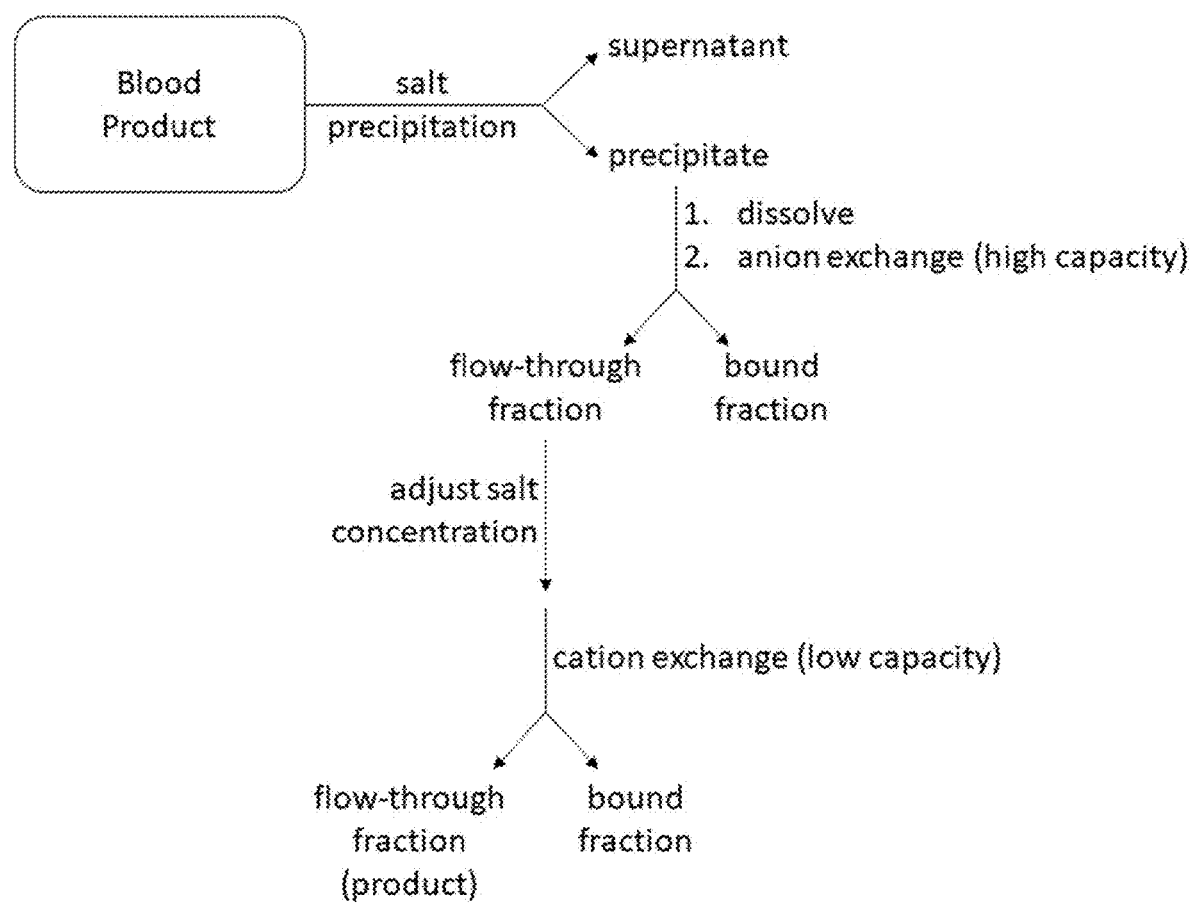
FIG. 11 schematically depicts an exemplary process of the inventive concept utilizing anion exchange and minimal cation exchange.

Although initial ion exchange steps in FIGS. 11 and 12 are shown utilizing an anion exchange step followed by application of the flow-through fraction to a low capacity cation exchange step (with subsequent recovery of the protein of interest from the cation exchange effluent), Inventors contemplate analogous methods that utilize an initial cation exchange step followed by application of the flow-through fraction to a low capacity anion exchange step and recovery of the protein of interest from the flow-through fraction from anion exchange. Such methods can be applied to isolation of non-IgG proteins.

Figure 13:
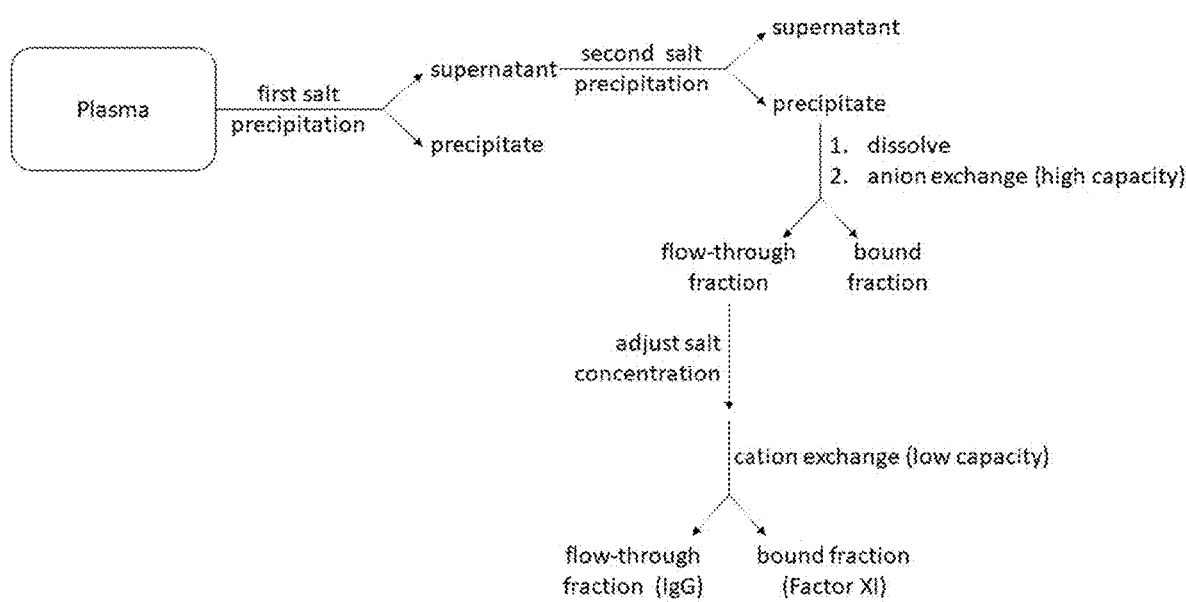
FIG. 13 schematically depicts an exemplary process of the inventive concept as applied to isolation of immunoglobulin G (IgG) from a blood product using anion exchange and restricted-capacity cation exchange.

Inventors have found methods of the inventive concept are particularly useful in the isolation of IgG from blood plasma, although application to other solutions containing IgG (e.g., cell culture media, cell lysates, other body fluids, etc.) is contemplated. Within the context of this application plasma is considered to include freshly collected plasma, refrigerated plasma, frozen plasma, cryo-poor plasma, and cryo-poor plasma into which the cryoprecipitate has been re-dissolved. Such plasma can, for example, be obtained from commercial collection centers. An example of a method of the inventive concept for isolation of IgG from plasma is shown in FIG. 13.

that prior art methods that utilize citrate precipitation in initial fractionation steps (such as those described in U.S. Pat. No. 7,879,331) were not useful at scales at which simple bag dialysis for buffer exchange became impractical (e.g., around 1 L or less). Inventors found that attempts to replace bag dialysis with diafiltration in order to support larger scale applications was impractical due to rapid fouling of diafiltration membranes, even though precipitated material may not be evident in the protein solutions being treated.

Towards that end Inventors have found that filtration can be used to remove residual undissolved or suspended material and/or material that precipitates following dissolving of the IgG-rich precipitate (e.g., on viral inactivation). Surprisingly, Inventors have found that the selection of filtration media used prior to ion exchange steps has a large effect on the concentrations of both IgG and undesired contaminants (e.g., Factor XI, Factor XII). Typical results of screening studies for filters useful in at-scale IgG isolation are shown in Table 7.

TABLE 7

| Filter | Filter material | Total protein (%) | [IgG], mg/mL | [Factor XI], ng/mL | [Factor XII], µg/mL | [ApoH], µg/mL |
|---|---|---|---|---|---|---|
| Starting material | Not applicable | 100% | 3.43 | 290 | 10.17 | 8.9 |
| F1 | Diatomaceous earth | 70% | 2.84 | 128 | 0.065 | 7.5 |
| F2 | Regenerated cellulose | 75% | 2.86 | 237 | 11.04 | Nondetectable |
| F3 | Regenerated cellulose | 78% | 3.08 | 200 | 11.26 | 7.7 |
| F4 | Perlite | 79% | 3.18 | 184 | 9.45 | 8.0 |
| F5 | Diatomaceous earth/Perlite | 71% | 2.98 | 146 | 9.15 | 6.7 |
| F6 | Diatomaceous earth/Perlite | 72% | 2.44 | 147 | 8.62 | Nondetectable |
| F7 | Diatomaceous earth/Perlite | 74% | 2.68 | 157 | 9.11 | 7.6 |
| F8 | Diatomaceous earth/Perlite | 72% | 2.78 | 177 | 9.15 | 7.3 |
| F9 | Silica | 54% | 2.62 | 60 | Nondetectable | Nondetectable |
| F10 | Diatomaceous earth/Perlite | 74% | 2.86 | 168 | 9.47 | Nondetectable |
| F11 | Quaternary amine/PES | 77% | 3.03 | 312 | 11.79 | 7.6 |

For the first two steps shown in FIG. 13 the Inventors modified and/or optimized a base fractionation process using a range of salt concentrations for two precipitation steps to determine the optimum concentrations (i.e., about 11% in the first salt precipitation and about 26% in the second salt precipitation) and to maximize IgG yield while minimizing unwanted proteins. Such salts can be added rapidly, as a salt solution (e.g., as a calculated volume of a 50% by weight salt solution) and/or in dry form (e.g., as a powder or crystalline solid). As shown, the first precipitation step produces an IgG-rich supernatant, and the second precipitation step produces an IgG-rich precipitate or paste. This IgG-rich precipitate is dissolved (e.g., in water) prior to ion exchange steps. As noted below, in preferred embodiments of such methods a buffer exchange step (e.g., dialysis, diafiltration, ultrafiltration followed by dilution, size exclusion chromatography, etc.) is not performed prior to ion exchange steps.

For an at-scale process to be successful, fouling of media used in processing steps (e.g., chromatography media) needs to be avoided. Such at-scale processes can utilize from about 500-600 L (e.g., for hyperimmune) to 8,000 L or more (e.g., for normal IgG) of plasma or serum. Applicants have found It is evident that fiber composition has an effect on retention of the desired IgG product on the filter material as well as retention of contaminants such as Factor XI and Factor XII. In particular, use of a diatomaceous earth depth filter (e.g., F1) shows minimal IgG retention (as a function of total protein) and marked reductions in both Factor XI and Factor XII contamination. In contrast, while silica F9 was found to effectively remove Factor XI and Factor XII, overall loss of protein content would negatively impact IgG yield. Similarly, while quaternary amine/PES filters retained little protein there was little or no retention of contaminating proteins.

Accordingly, in some embodiments of the inventive concept a depth filter that includes diatomaceous earth can be incorporated into an at scale IgG isolation process prior to an ion exchange step. In some of such embodiments the diatomaceous earth filter can be a depth filter. In some embodiments, a diatomaceous earth filter used in the method can exclude perlite. In some embodiments an additional particle filtration step (e.g., 1 µm, 0.45 µm, 0.2 µm pore filtration) can be performed after such a filtration step in order to reduce fouling of chromatography media in subsequent steps. In some embodiments size of the depth filter can be optimized to provide sufficient filter capacity and flux retention, while minimizing available surface area that can result in activation of Factor XI and/or Factor XII.

As shown in FIG. 6, in an IgG isolation process of the inventive concept the first ion exchange step can be performed using an anion exchange media. Such an anion exchange media can be a quaternary amine (Q) media. Such an anion exchange media can maintain a positive charge over a wide range of pH conditions (e.g., pH 1 to 14, pH 2 to 13, pH 3 to 12, pH 4 to 11). The anion exchange media can be provided on any suitable support (e.g., agarose, cross linked agarose, cellulose, polyacrylamide, polystyrene, glass, or combinations thereof) and in any suitable configuration (e.g., porous beads, non-porous beads, fibers, wools, filters, etc.).

In preferred embodiments of the inventive concept, the re-dissolved precipitate from the second precipitation step is not subjected to a buffer exchange process prior to application to anion exchange media. In the context of this application a buffer exchange process refers to a process in which salts are removed from the solution containing the protein of interest (e.g., IgG). Examples of such processes include, but are not limited to, dialysis, diafiltration, concentration by ultrafiltration followed by dilution, and size exclusion chromatography. Such buffer exchange processes do not include simple dilution of non-concentrated re-dissolved precipitate, which retains salts present in the protein solution. Since the protein of interest (e.g. IgG) is recovered in flow-through fractions of the ion exchange steps, it is preferred that if dilution is performed it is done so using a minimal volume (e.g., less than 3× the original volume, about 1.5× to 2.5× the original volume, about 2× the original volume, about 1.5× the original volume, or with about the original volume) of diluent.

As shown in FIG. 6, in an at-scale IgG process of the inventive concept IgG is recovered in the flow-through (i.e., unbound) fraction from the anion exchange media. This first flow-through fraction is subsequently applied to a small or low capacity cation exchange media (e.g., media that includes carboxylate or sulfonate groups) in which size/capacity, and buffer conditions have been selected such that contaminating proteins are retained while IgG (which typically also binds to cation exchange media) passes through in the flow-through fraction (i.e., the second flow-through fraction). Typically, the capacity or size of the cation exchange media is selected to be at or slightly exceeding by 1%, 2%, 5%, 10%, 15%, 20%, 25%, 30%, 50%, 75%, or 1.00%) its capacity for contaminants present in the first flow-through fraction. Without wishing to be bound by theory, Inventors believe that when a cation exchange media and binding conditions are so selected the IgG is displaced by contaminating protein and so remains in the second flow-through fraction, thereby increasing yield over methods in which IgG is bound and then eluted. In preferred embodiments loss of IgG in the cation exchange step is less than about 10%, 8%, 6%, 5%, 4%, 3%, 2%, or 1% of IgG content of the starting material.

Such cation exchange media can be provided on any suitable support agarose, cross linked agarose, cellulose, polyacrylamide, polystyrene, glass, or combinations thereof) and in any suitable configuration (e.g., porous beads, non-porous beads, fibers, wools, filters, etc.). Inventors have found that the capacity of the cation exchange media utilized can be quite small, and in preferred embodiments can be provided by a filter with pendant cation exchange groups. This advantageously combines purification and clarification steps.

In some embodiments of the inventive concept the buffer composition, conductivity, and/or pH of the first flow-through fraction can be modified prior to application to the cation exchange media in order to optimize capacity and selectivity for contaminants. In preferred embodiments salts can be added to increase the ionic strength or conductivity of the first flow-through fraction to fall within a desired range.

In some embodiments the second flow-through fraction can be subjected to additional processing steps. Such additional processing steps can include nanofiltration for virus removal, such as filtration using a 0.02 μm pore membrane. Inventors have found that this effectively retains any remaining virus particles while minimizing yield losses.

In some embodiments the purified protein solution can be prepared for use by concentration and diafiltration in order to provide a drug product having a useful concentration in a pharmacologically compatible buffer that provides stability. For IgG, such a step can provide an IgG concentration of, for example, about 4% to 6% IgG (w/v) or greater in a suitable formulation buffer (e.g., 0.2M glycine pH 4.2 to pH 6.5) with minimal losses. Concentration can be increased or otherwise adjusted using known methods.

Typical IgG yield results for an IgG isolation process of the inventive concept are shown in Table 8.

TABLE 8

Total yield based on $A_{280}$ absorbance/initial nephelometry values corrected for sample removal. Extinction Coefficient for IgG: 1.3

| Sample | Concentration (A280/mL) | Volume (mL) | Total (A280) | Total IgG [A280] (mg) | IgG [Neph] (mg/mL) | Total IgG [Neph] (mg) | IgG Yield (%) |
|---|---|---|---|---|---|---|---|
| Cryo-poor Plasma | 44.41 | 2000 | 88820 | N/A | 8.25 | 16500 | 100.0 |
| First Supernatant | 35.62 | 2490 | 88693.8 | | 6.34 | 15786.6 | 95.7 |
| First Precipitate | N/A | 22.9 g | N/A | | | N/A | |
| Second Supernatant | 14.07 | 3850 | 54169.5 | | | | |
| Second Precipitate | N/A | 187 g | N/A | | | | |
| Dissolved Second | 14.73 | 2000 | 29460 | N/A | 7.33 | 14660 | 88.8 |

TABLE 8-continued

Total yield based on $A_{280}$ absorbance/initial nephelometry values corrected for sample removal. Extinction Coefficient for IgG: 1.3

| Sample | Concentration (A280/mL) | Volume (mL) | Total (A280) | Total IgG [A280] (mg) | IgG [Neph] (mg/mL) | Total IgG [Neph] (mg) | IgG Yield (%) |
|---|---|---|---|---|---|---|---|
| Precipitate Post Depth Filter | 10.47 | 2570 | 26907.9 | N/A | 5.86 | 15060.2 | 91.3 |
| Post 0.2 μm Filter | 6.37 | 4284 | 27289.08 | N/A | 3.49 | 14951.16 | 90.6 |
| Anion Exchange Flow-Through | 2.63 | 5680 | 14938.4 | N/A | 2.3 | 13064 | 79.2 |
| Cation Exchange Flow-Through | 2.52 | 5930 | 14943.6 | 11495 | 2.13 | 12630.9 | 76.6 |
| Post Nano-Filtration | 2.24 | 6107 | 13679.68 | N/A | | N/A | |
| Final Product | 67.11 | 248 | 16643.28 | 12802 | N/A | N/A | 77.6 |
| Total Additive Loss from Sample Removal | | | | | | 0.96 | |

Test results obtained from the material shown in Table 8 met all release criteria for commercial IgG product. The results are Table 9 and Table 10.

| Test | Result | Pass/Fail | EP Standard |
|---|---|---|---|
| PKA | 1.48 IU/mL | Pass | <35 IU/mL |
| IgA | 1.57 μg/mL | N/A | "Not more than is stated on the product label" |
| IgM | Not Detectable | N/A | No EP standard |
| IgG subclass | IgG 1  IgG 2  IgG 3  IgG 4 | | Product should be representative of starting material |
| Starting Material | 62   28   7   4 | | |
| Finished Product | 62   30   7   1 | | |
| Fc function | 119% | Pass | >60% |
| ACA | 0.83 CH50U/mg | Pass | ≤1.5 CH50U/mg |
| NaPTT | 219.5 sec | Pass | >200 sec |
| FXIa (chromogenic) | <0.04 mU/mL | Pass | No EP standard |
| FXIa (eCAT/TGA) | 0.79 mU/mL | Pass | No EP standard (<1 mU/mL historically in prior art) |

TABLE 10

| Test Method | | Result | Acceptance Criteria (ACC) |
|---|---|---|---|
| SE-HPLC | % Dimer | 2.149 | Mono- & dimeric ≥90% |
| | % Monomer | 97.361 | Polymeric <2% |
| | % IGIV | 99.510 | Fragment <3% |
| | % Polymeric (HMW) | 0.338 | |
| | % Fragment (LMW) | 0.152 | |

In addition to remarkably low levels of Factor XI contamination, the Inventors have found that methods of the inventive concept provide surprisingly low levels of IgA contamination.

The methods described above are robust and commercially scalable processes that consistently produce about a 72-85% yield of IgG (relative to IgG content of the starting material) from starting plasma in just 24 to 72 hours (preferably about 48 hours). The resulting product is >99% pure IgG product with 100% functionality.

It should be appreciated that additional plasma proteins can be recovered from various intermediate waste streams generated by methods of the inventive concept, for example the precipitate generated in the first fractionation step, the supernatant generated in the second fractionation step, the bound fraction from the anion exchange step, and/or the bound fraction from the cation exchange step. In some embodiments two or more of such intermediate product streams can be combined as a source of a non-IgG plasma protein to be isolated. Such intermediate products can be treated by any suitable method (e.g., additional precipitation steps, affinity chromatography, size exclusion chromatography, hydrophobic interaction chromatography, ion exchange chromatography, and/or mixed mode chromatography) to facilitate isolation of additional non-IgG proteins from the starting material.

Inventors believe that the citrate precipitation steps are gentler than prior art ethanol precipitation processes and minimize the risk of protein denaturation since the IgG product is produced without alcohol, extreme pH changes, numerous and prolonged exposures to extreme temperatures and lengthy processing times. The avoidance of alcohol and low pH has implications for improved protein stability, in vivo half-life, immunogenicity of the protein therapeutics, patient tolerability, and faster infusion rates.

The Inventors' process is also environmentally friendly (salt vs. alcohol) and more cost-effective than Cohn fractionation-based processes.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method for isolating a target protein from a solution comprising the target protein and a plurality of contaminants, comprising:
    adding a salt to the solution to generate a supernatant and a precipitate;
    dissolving the precipitate in an aqueous solution to generate a dissolved precipitate comprising the target protein and a first portion of the plurality of contaminants;
    applying the dissolved precipitate to a first ion exchange media having a first charge with a first polarity under first buffer conditions selected to not bind the target protein to generate a first bound fraction comprising a second portion of the plurality of contaminants and a first flow-through, wherein the first flow-through comprises the target protein and a third portion of the plurality of contaminants;
    preparing a second ion exchange media selected to bind both the target protein and a fourth portion of the plurality of contaminants under second buffer conditions, wherein the second ion exchange media comprises a second charge with a second polarity that is opposite that of the first polarity;
    applying the first flow-through to the second ion exchange media under second buffer conditions to generate a second bound fraction comprising the fourth portion of the plurality of contaminants and a second flow-through comprising the target protein;
    wherein preparing comprises selecting a limited capacity of the second exchange media such that greater than 70% of content of the target protein in the solution is recovered in the second flow-through.

2. The method of claim 1, wherein the solution is plasma.

3. The method of claim 1, wherein the solution is a product of a separation step.

4. The method of claim 1, wherein the first ion exchange media is an anion exchange media, the second ion exchange media is a cation exchange media, and the target protein is immunoglobulin G.

5. The method of claim 1, wherein the plurality of contaminants comprises Factor XI or activated Factor XI.

6. The method of claim 1, wherein the first ion exchange media is configured as a particle or bead.

7. The method of claim 1, wherein the second ion exchange media is configured as a filter.

8. The method of claim 1, further comprising adding caprylate to the dissolved precipitate to form a treated dissolved precipitate.

9. The method of claim 8, comprising removing solids from the treated dissolved precipitate following addition of caprylate.

10. The method of claim 9, comprising removing solids from the treated dissolved precipitate by performing a filtration step that comprises passage through a filter to the treated dissolved precipitate, wherein the filter comprises a material that selectively retains Factor XI or Factor XII.

11. The method of claim 10, wherein the filter does not include perlite.

12. The method of claim 1, wherein yield of the target protein in the second flow-through is at least 90%.

13. The method of claim 12, wherein the salt is a citrate or acetate salt.

14. The method of claim 1, comprising recovering at least one additional protein from the supernatant.

15. The method of claim 1, wherein the volume of the solution is at least 500 L.

16. A method of improving tolerance and increasing infusion rate for a therapeutic protein, comprising:
    isolating the therapeutic protein by a method of claim 1, wherein the therapeutic protein has a purity of at least 95% and has not been subjected to denaturing conditions; and
    providing the therapeutic protein for infusion.

17. The method of claim 16, wherein the therapeutic protein is IgG.

18. The method of claim 1, wherein greater than 80% of content of the target protein in the solution is recovered in the second flow-through.

* * * * *